(12) United States Patent
Bleifuβ et al.

(10) Patent No.: US 9,012,697 B2
(45) Date of Patent: Apr. 21, 2015

(54) PROCESS FOR PREPARING ALKYLATED HYDROXYAROMATICS IN MICROREACTORS

(75) Inventors: Oliver Bleifuβ, Scheneverdingen (DE);
Simon Rost, Büchen (DE);
Klaus-Wilhelm Lienert, Hamburg (DE);
Hans-Ulrich Moritz, Bendedorf (DE)

(73) Assignee: Elantas GmbH, Wesel (DE)

( * ) Notice: Subject to any disclaimer, the term of this patent is extended or adjusted under 35 U.S.C. 154(b) by 189 days.

(21) Appl. No.: 13/413,868

(22) Filed: Mar. 7, 2012

(65) Prior Publication Data

US 2012/0238783 A1   Sep. 20, 2012

(30) Foreign Application Priority Data

Mar. 8, 2011   (DE) .......................... 10 2011 005 228

(51) Int. Cl.
| | | |
|---|---|---|
| *C07C 37/48* | (2006.01) | |
| *H01B 3/30* | (2006.01) | |
| *C07C 37/16* | (2006.01) | |
| *H01B 3/20* | (2006.01) | |

(52) U.S. Cl.
CPC ................ *H01B 3/308* (2013.01); *C07C 37/16* (2013.01); *H01B 3/20* (2013.01)

(58) Field of Classification Search
CPC ............................... C07C 2/66; B01J 19/0093
USPC ......................................... 568/804, 785, 902
See application file for complete search history.

(56) References Cited

U.S. PATENT DOCUMENTS

| | | | |
|---|---|---|---|
| 3,290,389 A | 12/1966 | Hahn | |
| 3,367,981 A | 2/1968 | Napolitano | |
| 3,855,318 A | 12/1974 | Nakajima et al. | |
| 3,867,466 A | 2/1975 | Endou et al. | |
| 4,714,691 A * | 12/1987 | Goins et al. ................... | 502/152 |
| 5,128,304 A * | 7/1992 | Ito ............................... | 502/242 |
| 5,371,306 A * | 12/1994 | Woo et al. ..................... | 568/804 |
| 5,534,328 A | 7/1996 | Ashmead et al. | |
| 5,690,763 A * | 11/1997 | Ashmead et al. ............... | 156/60 |
| 5,811,062 A | 9/1998 | Wegeng et al. | |
| 5,847,237 A * | 12/1998 | Yago et al. ..................... | 568/804 |
| 7,304,198 B2 * | 12/2007 | Wang et al. .................... | 585/716 |
| 2008/0114192 A1 * | 5/2008 | Patel et al. ..................... | 568/790 |

FOREIGN PATENT DOCUMENTS

| | | |
|---|---|---|
| CN | 10154145 A | 8/2009 |
| DE | 1 668 880 | 9/1971 |
| DE | 2 127 083 | 12/1971 |
| DE | 2 161 252 | 9/1972 |
| GB | 717588 | * 10/1954 |
| GB | 1034500 | 6/1966 |
| GB | 1065337 | 4/1967 |

OTHER PUBLICATIONS

Zapf et al., "Detailed Characteriztion of Various Porous Alumina-Based Catalyst Coatings Within Microchannels and Their Testing for Methanol Steam Reforming", Trans IChemE, vol. 81, Part A, Aug. 2003, pp. 721-729.

* cited by examiner

*Primary Examiner* — Sudhakar Katakam
*Assistant Examiner* — Pancham Bakshi
(74) *Attorney, Agent, or Firm* — Birch, Stewart, Kolasch & Birch, LLP

(57) ABSTRACT

A process is proposed for preparing hydroxyaromatics by heterogeneous catalytic reaction of hydroxyaromatics with $C_1$-$C_4$-alkanols in a microreactor (10), comprising the steps of:
  a) introducing the hydroxyaromatic and at least one compound selected from the group consisting of $C_1$-$C_4$-alkanols as reactants into at least one inlet orifice (22) of the microreactor (10) comprising at least one microreactor unit (18),
  b) passing the reactants through at least one microreactor unit (18) of the microreactor (10), said unit comprising a multitude of microchannels (28), said microchannels (28) having a lateral extent of less than 1 mm, and a heterogeneous catalyst being incorporated in the microchannels (28) for conversion of the reactants,
  c) passing the hydroxyaromatics prepared out through at least one outlet orifice (24) of the microreactor (10).

6 Claims, 2 Drawing Sheets

US 9,012,697 B2

PROCESS FOR PREPARING ALKYLATED HYDROXYAROMATICS IN MICROREACTORS

Figure 1:
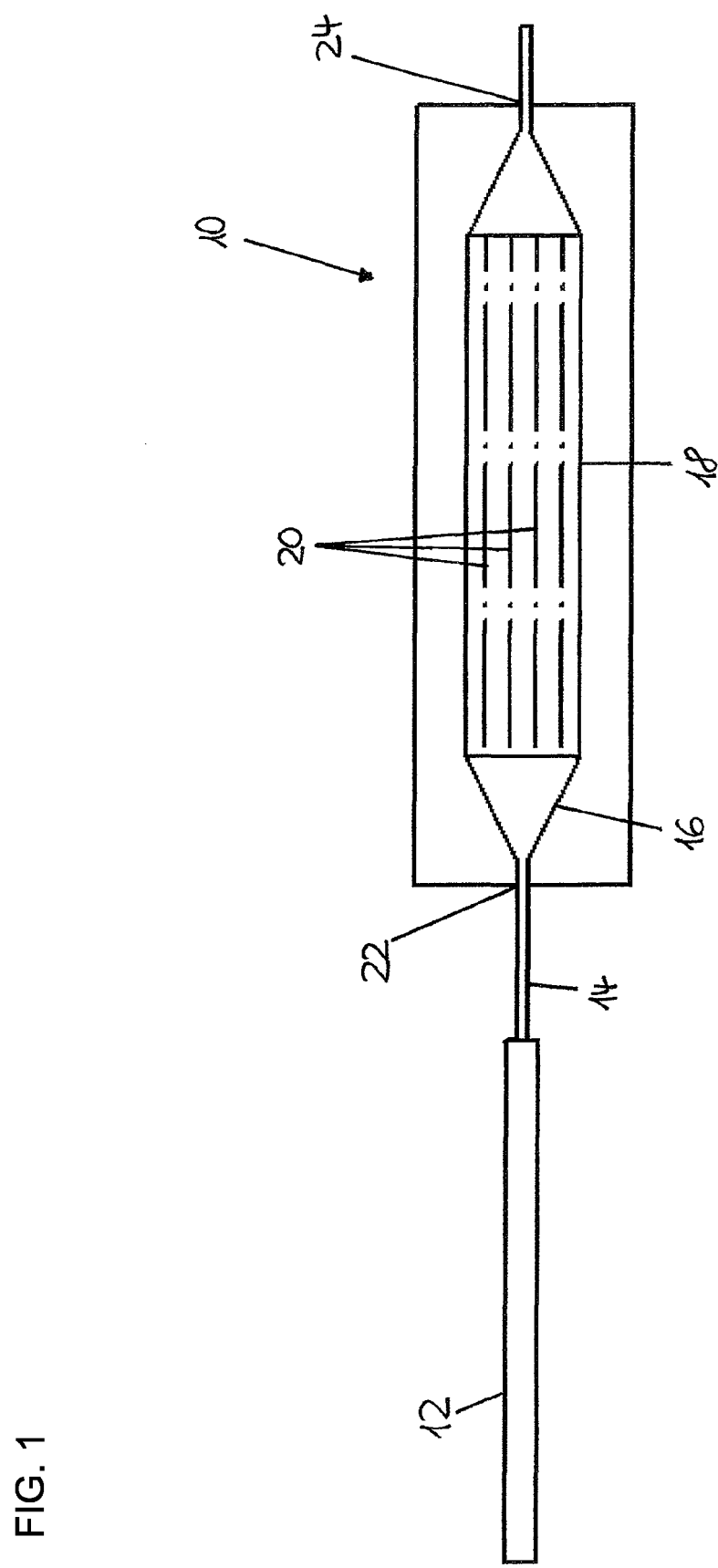

The invention relates to a process for preparing alkylated hydroxyaromatics by heterogeneous catalytic reaction of hydroxyaromatics with $C_1$-$C_4$ alkanols. The invention further relates to the use of the alkylated hydroxyaromatics prepared by means of the process according to the invention as a solvent in wire enamel compositions.

Phenol and the alkyl derivatives thereof, for example cresols, xylenols and anisoles, are of particular significance for the production of synthetic resins and enamels. In electrical engineering, these compounds are regularly used for enamels which are particularly suitable for electrical insulation of copper and aluminium wires. These wire enamels therefore have to meet many demands at the same time. They should have a high chemical and thermal stability, good adhesion on wires, and particularly good mechanical strength. Due to the high material demands, there is therefore a need for constant improvement in the material properties of the wire enamels used.

Alkylated hydroxyaromatics, as used as solvents for wire enamels, are prepared typically in conventional reactor types such as tube/shell-and-tube or fluidized bed reactors. In this type of reactors, the catalyst is typically in the form of a fixed bed, moving bed or fluidized bed. According to the catalyst used, alkylated hydroxyaromatics are prepared in conventional reactors at high temperatures or under high pressure in order to achieve a better space-time yield.

GB 1 065 337, for example, describes an alkylation process by means of alkanol, preferably methanol or ethanol, the reaction components being passed in a molar ratio of 0.6:1 to 0.8:1 in the gas phase over an optionally activated alumina catalyst. One example described is that of obtaining o-cresol in yields averaging 27.3% by mass, with simultaneous formation of 12.4% by mass of 2,6-dimethylphenol and 5.0% by mass of other phenols.

In DE 1 668 880, a mixture of phenol and methanol (10% by mass of methanol) is passed at 250 to 350° C. and a liquid hourly space velocity (LHSV) of 0.5 ($h^{-1}$) over a customary alumina catalyst with a specific surface area (BET) of 240 $m^2$/g to obtain a product mixture of 22% by mass of o-cresol, 5% by mass of 2,6-dimethylphenol and traces of anisol. Tests showed that, as well as these products, further methylation products of phenol, such as m-, p-cresol, di- and trimethylphenols, are obtained, the amount of which is approx. 2% by mass. In this case, a tubular reactor is used with an external diameter of 20 mm and a length of 1 mm.

GB 1 034 500 describes the alkylation reaction in a fixed bed reactor using magnesium oxide as a catalyst. However, high reaction temperatures of 475 to 600° C. are required here, at which significant decomposition of the starting materials, for example of the phenol and methanol, already occurs. A further disadvantage lies in the rapid decline in activity and the short service life of the catalyst.

The use of mixed catalysts, such as vanadium/iron oxide or cerium oxide/manganese oxide, for the alkylation of phenols is proposed in DE 2 161 252 and in DE 2 127 083. These catalyst types, however, exhibit relatively low reactivity, and so a high excess of alkylating agent (e.g. methanol) is required even for the production of monoalkylated products, and, moreover, relatively high temperatures and relatively low throughputs have to be employed. For instance, according to DE 2 127 083, the o-cresol synthesis is effected at 400° C. and an LHSV of 0.3, the ratio of by-products (e.g. 2,6-dimethylphenol) to o-cresol being 0.38. Conventional tubular reactors are used here for the gas phase reactions.

U.S. Pat. No. 3,290,389 and U.S. Pat. No. 3,367,981 describe processes in which aluminium catalysts are used for alkylation of phenols. They describe substitution taking place essentially in the ortho position. The reactions described in these documents are performed at temperatures above 250° C. in pressure vessels. CN 101514145 describes a further synthesis process for o-cresol. This process is characterized by the following steps: mixing of phenol and methanol in a mass ratio of 1:(0.5-4), conveying the mixture into a tubular reactor comprising the catalyst, introducing an inert carrier gas into the reactor, and finally condensing and separating the reaction products. The reactions are performed at standard pressure and temperatures of 280 to 450° C.

It is also known that cresols can be obtained as by-products in the synthesis of dimethylphenols and the subsequent isolation of the o-cresol by additional purification steps. Processes for obtaining o-cresol are described in Frank/Stadelhofer INDUSTRIELLE AROMATENCHEMIE: Rohstoffe, Verfahren, Produkte [INDUSTRIAL AROMATIC CHEMISTRY: Raw Materials, Processes, Products], Springer Verlag, Berlin 1987.

The known processes for preparing alkylated hydroxyaromatics are performed predominantly in conventional reactors. In these reactors, it is difficult due to the dimensions to establish a homogeneous thermal distribution over the reactor volume. This increases the risk of exposing the catalyst to excessive thermal stress, which influences the catalyst performance and the catalyst lifetime.

In addition, the production of alkylated hydroxyaromatics on an industrial scale is found to be difficult. This is because the upscaling of chemical processes to the industrial production scale presents the fundamental problem that the dimensions of the production plants are several orders of magnitude greater than the equipment used to develop the processes on the laboratory scale. Due to the production volumes required on the industrial scale, conventional chemical reactors usually have dimensions between a few centimeters up to a few meters in size. Therefore, the findings regarding the process regime obtained on the laboratory scale cannot be applied directly to the industrial scale. Even in the course of mixing of liquids, a stirrer system is needed preliminary for the purpose of increasing mass transfer by reducing the distances between areas of different concentration.

The different dimensions of the reactors give rise to what is called the scaleup problem. A chemical reaction which has been optimized on the laboratory scale is not then immediately upscaled to the production plant, but instead first tested on a pilot plant with dimensions between the laboratory scale and the production scale, before it is finally used in industrial scale production. A problem here is that each stage of this process development requires a dedicated optimization cycle, each of these cycles forming part of the sum total of development time required for the process introduction.

In spite of extensive prior art in the field of preparation of alkylated hydroxyaromatics, there is a constant need for optimization with regard to higher space-time yields in order to make the chemical processes more efficient. Accordingly, it was an object of the invention to provide a process for preparing alkylated hydroxyaromatics, which has a higher space-time yield. The process shall also provide a product which can be used especially for wire enamels.

This object is achieved by a process for preparing hydroxyaromatics by heterogeneous catalytic reaction of hydroxyaromatics with $C_1$-$C_4$-alkanols in a microreactor, comprising the steps of:
a) introducing the hydroxyaromatic and at least one compound selected from the group consisting of $C_1$-$C_4$-alkanols as reactants into at least one inlet orifice of the microreactor comprising at least one microreactor unit,
b) passing the reactants through at least one microreactor unit of the microreactor, said unit comprising a multitude of microchannels, said microchannels having a lateral extent of less than 1 mm, and a heterogeneous catalyst being incorporated in the microchannels for conversion of the reactants,
c) passing the hydroxyaromatics prepared out through at least one outlet orifice of the microreactor.

A hydroxyaromatic in the context of the present invention has at least one aromatic ring to which at least one hydroxyl group is bonded. Correspondingly, an alkylated hydroxyaromatic has an aromatic ring to which at least one alkyl group is additionally bonded.

A microreactor as used in the process according to the invention comprises at least one inlet orifice connected via at least one microreactor unit to at least one outlet orifice. The at least one microreactor unit, in which the chemical reaction takes place, of the microreactor comprises a multitude of microchannels with a lateral extent of less than 1 mm. The lateral extent refers in this context to the dimensions of a microchannel in a plane at right angles to the microchannel axis. In addition, a heterogeneous catalyst is incorporated into the multitude of microchannels.

The process according to the invention advantageously uses such a microreactor to prepare alkylated hydroxyaromatics. Thus, a stream is passed through a multitude of microchannels in the microreactor comprising a microreactor unit. With a lateral extent of less than 1 mm, the microchannels have a volume to surface ratio which allows better control of process parameters than in the case for conventional reactors, for example shell-and-tube reactors. Thus, due to the lateral extent of each microchannel of less than 1 mm, and accordingly the low volume flow in each microchannel, optimal heat and mass transfer is achieved. This allows, more particularly, control of the temperature in each microchannel and of the temperature of the stream in each microchannel. This is particularly advantageous for the process according to the invention, which is based on heterogeneous catalysis and which envisages the heterogeneous catalyst in the multitude of microchannels, since decomposition of the catalyst can be prevented by the temperature control.

In addition, by virtue of the small dimensions of the microchannels, local differences in the concentration and temperature of the stream are reduced to a minimum degree. This allows the process according to the invention to be adjusted to optimal boundary conditions, such that the conversion rates of alkylated hydroxyaromatics can be increased as in conventional reactors with the same residence time. Alternatively, similar conversion rates to those in conventional reactors can be achieved with reduced residence time. In addition, the purity and the yield of alkylated hydroxyaromatics are also optimized through the adjustable process conditions. In this way, the process according to the invention provides alkylated hydroxyaromatics, which surprisingly have excellent solvent properties for wire enamels.

In addition, the use of the microreactor in the process according to the invention for preparation of alkylated hydroxyaromatics avoids problems which arise in the scaleup of the process from a laboratory scale to industrial large-scale production. For instance, the volume flow rate in an individual microchannel is low due to the lateral dimension. For a multitude of microchannels, however, the volume flow rates of the individual microchannels add up. In this way, it is possible with a microreactor, in spite of the small dimensions of the microchannels, to achieve a large volume flow rate overall, and scaleup from the laboratory scale to industrial large-scale production can be effected by simple replication of the microchannels.

Microreactor

The microreactor used in the process according to the invention may, as well as the at least one microreactor unit in which the chemical reaction takes place, comprise further functional units which exert additional functions in the chemical process regime. The configuration of such functional units is described, for example, in U.S. Pat. Nos. 5,534,328, 5,811,062 or 5,690,763. For instance, at least one unit can be provided for mixing of the reactants between the inlet orifice of the microreactor and the at least one microreactor unit in which the chemical reaction takes place. Alternatively, the inlet orifice of the microreactor may have an external mixer connected upstream, which mixes the reactants even before they are supplied to the microreactor. In general, the reactants are, or the reactant mixture is, supplied by means of a metering pump which regulates the flow rate and the pressure in the microreactor.

In addition, at least one unit of the microreactor may be configured as a heat exchanger in order to supply heat to an adjacent microreactor unit, or to remove it from an adjacent microreactor unit. In this way, the temperature in individual microreactor units can be controlled according to the intended function thereof in the chemical process regime. In one embodiment, the temperature in the at least one microreactor unit in which the chemical reaction takes place is controlled by adjacent heat exchanger units. In a preferred embodiment, the temperature in the at least one microreactor unit in which the chemical reaction takes place is controlled in a simple manner by external heating elements, for example by heating collars or heating cartridges. The temperature is measured regularly by means of temperature sensors, which may be mounted, for example, on a microreactor unit and on an outlet of the microreactor.

To form the microchannels in at least one microreactor unit, as described, for example, in U.S. Pat. No. 5,534,328, microstructured plates are used. These are preferably manufactured from a material with high thermal conductivity, for example steel or silicon. To form the microstructured plates, a multitude of recesses are introduced into the plates, which, according to the desired profile of the microchannels, may be semicircular, oval, trapezoidal or rectangular in shape. These recesses can be introduced into the plates either on one side or on both sides by means of known processes, such as milling, wet etching or diamond cutting. To form a multitude of microchannels, the microstructured plates can be stacked directed facing one another such that the multitude of complementary recesses forms a multitude of microchannels.

The at least one microreactor unit is accordingly formed from at least two plates which lie one on top of the other and have surface recesses which form the microchannels. Preferably, a microreactor unit is formed from 2 to 10 plates lying one on top of another. The structure of the recesses introduced into the microstructured plates thus determines the three-dimensional geometry of the multitude of microchannels. According to the profile of the recesses, these microchannels have a maximum lateral extent of less than 1 mm, preferably between 0.1 and 0.8 mm. Particular preference is given to a maximum lateral extent, according to the profile of the recesses, of between 0.4 and 0.6 mm. The numerical values here are based on the maximum lateral extent at right angles to the flow direction.

The stacked microstructured plates generally comprise integrated sealing zones which bring about a liquid-tight and gas-tight connection between the microstructured plates and to the outside. The sealing material used may, for example, be graphite. The stacked microplates may also be surrounded by a housing of appropriate size, such that the sealing zones of the microstructured plates adjoin one another with sealing by virtue of sufficient applied pressure. The assembly of two or more plates accordingly forms a microreactor unit which, according to the structure of the multitude of microchannels, can be configured as a functional unit or as a microreactor unit in which the chemical reactions take place. In addition, orifices which allow mass flow through the microreactor unit are provided in a microreactor unit.

In one embodiment of the microreactor as used in the process according to the invention, the microchannels are in the form of straight channels running from an inlet orifice to an outlet orifice. The length of the microchannels is 50 mm to 150 mm. This configuration is simple to produce and does not require any special precautions for production of the microstructured plates. In addition, a single inlet orifice of a microreactor unit may be configured with straight microchannels such that all microchannels are supplied from one stream. This configuration has the advantage that there is no need to provide any further inlet orifices with external supply elements, for example a metering pump, a mixer or a preheater.

Reactants

Hereinafter, the reactants which serve for preparation of alkylated hydroxyaromatics by the process according to the invention are elucidated in detail.

For performance of the process according to the invention, the reactants may be in the liquid phase, in the gaseous phase or in biphasic form. The individual reactants need not necessarily be supplied in the same phase to the microreactor. The reactants may also be mixed or preheated directly within or outside the microreactor. This has the advantage of resulting in increased flexibility in the supply of the reactants to the microreactor, and that there is no need to provide any further process steps or additional measures in order, for example, to introduce the two reactants into the microreactor in the same phase.

The hydroxyaromatic used, which is reacted as a reactant with $C_1$-$C_4$-alkanols in the presence of a heterogeneous catalyst in the microchannels, is typically at least one phenol compound having at least one aromatically bonded hydrogen atom. The at least one phenol compound is preferably selected from the group consisting of phenol, o-cresol, m-cresol, p-cresol, xylenols, trimethylphenols, tetramethylphenols, ethylphenols, diethylphenols, triethylphenols, iso-propylphenols, di-iso-propylphenols, tri-iso-propylphenols, tetra-iso-propylphenols, n-propylphenols, di-n-propylphenols, tri-n-propylphenols, tetra-n-propylphenols, tert-butylphenols, di-tert-butylphenols, tri-tert-butylphenols and tetra-tert-butylphenols. A particularly preferred phenol compound is phenol.

The $C_1$-$C_4$-alkanols used in the process according to the invention may be individual $C_1$-$C_4$-alkanols or mixtures thereof. The reactant may accordingly comprise a composition of $C_1$-$C_4$-alkanols of the same or different carbon number. In addition, it is possible to use $C_1$-$C_4$-alkanols with a homogeneous number of carbon atoms and/or mixtures of $C_1$-$C_4$-alkanols with a different number of carbon atoms. These also include mixtures of different isomers of $C_1$-$C_4$-alkanols with the same carbon number. Preference is given to $C_1$-$C_3$-alkanols. The $C_1$-$C_4$-alkanols used are more preferably methanol, ethanol, n-propanol, isopropanol or mixtures thereof. The $C_1$-$C_4$-alkanols used are most preferably methanol, ethanol or 2-propanol.

Catalyst

The microreactor in which the process according to the invention is performed provides at least one microreactor unit in which the chemical reaction takes place. For this purpose, this microreactor unit comprises a multitude of microchannels which comprise the heterogeneous catalyst for conversion of the reactants. The heterogeneous catalysts used may be all catalysts suitable for preparation of alkylated hydroxyaromatics, optionally with a suitable support material. Preference is given to using those catalysts which are suitable for alkylation of phenol.

In one embodiment, the heterogeneous catalyst is introduced as a solid catalyst into the multitude of microchannels of the microreactor. In this case, the heterogeneous catalyst may be in crystalline, microporous and/or mesoporous form. In the case of an unsupported catalyst, which consists essentially of the active component, the heterogeneous catalyst may preferably be in the form of a coating on the walls of the microchannels. In this case, according to the nature and properties of the heterogeneous catalyst, different coating processes known to those skilled in the art can be used, for example chemical gas phase deposition (chemical vapour deposition, CVD) or physical gas phase deposition (physical vapour deposition, PVD for short).

In a further embodiment, the heterogeneous catalyst comprises a solid support, which preferably comprises one or more components from the group consisting of inorganic oxides, carbon, polymers, clay, zeolites or mesoporous solids. The inorganic oxides used are, for example, silicon oxide, aluminium oxide, zinc oxide and titanium oxide. Typical mesoporous solids are, for example, the commercially available MCM-41 or MCM-48, where MCM stands for Mobile Crystalline Matter. For the process according to the invention, a suitable solid support is provided in the multitude of microchannels present in the at least one microreactor unit for catalytic conversion. In the selection of a suitable support material, according to the configuration of the process according to the invention, aspects such as the size of the surface provided, the number of pores or the thermal stability, for example, should be taken into account.

The heterogeneous catalyst may also comprise an active component on the support. Advantageously, the heterogeneous catalyst is introduced into the microchannels by wash-coating the plates and optionally impregnating the washcoat with an active component. Preference is given to providing a support material composed of inorganic oxides, by coating the microchannels with a washcoat, preferably by applying a liquid suspension, and then impregnating the washcoat, if appropriate, with the active component. Such a process is described, for example, in R. Zapf, C. Becker-Willinger, K. Berresheim, H. Bolz, H. Gnaser, V. Hessel, G. Kolb, P. Löb, A.-K. Pannwitt, A. Ziogas, Trans IchemE, Vol 81, Part A, 2003, 721-729. For this purpose, a suspension is applied to the microstructured plates in such a way that exclusively the microchannels are coated. This coating is dried at room temperature and optionally calcined at temperatures between 500 and 600° C. In the course of calcination, unwanted additives, for example binders, are burnt off.

Thereafter, the active component of the heterogeneous catalyst is introduced into the coating, typically by means of impregnation. The impregnation may be followed by further drying at 50 to 500° C., preferably at 100 to 200° C., at a pressure below or at atmospheric pressure (~1013 bar). This may be followed by a further calcination at temperatures between 400 and 1500° C., preferably between 500 and 600° C. The drying and optional calcination serve to activate the catalyst, calcination being especially advantageous in the case of preparation of metal oxide catalysts, for example alumina or silica. In this way, it is possible to produce catalysts whose properties, for example regeneratability, abrasion resistance, reproducibility of production, are adjustable. The production may also lead to low costs.

The process according to the invention is performed preferably at a temperature of 300 to 600° C. and preferably of 350 to 500° C. In the case of use of alumina as a heterogeneous catalyst, a temperature between 400 and 500° C. has been found to be particularly advantageous. The temperature mentioned is understood to mean the temperature in the microreactor unit in which the catalytic reaction takes place. For the $C_1$-$C_4$-alkanols used too, there are preferred temperature ranges. For methanol, for example, the process according to the invention is performed preferably at a temperature of 400 to 550° C. and more preferably 450 to 500° C. In the case of use of ethanol, the process according to the invention is executed preferably at a temperature of 350 to 500° C. and more preferably 400 to 450° C. For 2-propanol, the temperature for performance of the process according to the invention is preferably between 330 and 430° C. and more preferably between 350 and 390° C.

Product

In the process according to the invention, alkylated hydroxyaromatics are prepared, preferably alkylated phenol compounds. The process according to the invention is preferably used to prepare cresols, xylenols, ethylphenols, isopropylphenols, trimethylphenols, tetramethylphenols, pentamethylphenols, diethylphenols, triethylphenols, tetraethylphenols, pentaethylphenols, di-iso-propylphenols, tri-iso-propylphenols, tetra-iso-propylphenols, penta-iso-propylphenols, ethylmethylphenols, methylpropylphenols and ethylpropylphenols. Particular preference is given to the preparation of o-cresol, m-cresol, p-cresol, 2-ethylphenol, 2,6-xylenol or 2-isopropylphenol.

Alkylated hydroxyaromatics prepared by the process according to the invention surprisingly have excellent solvent properties, which lead, for example, to a clear enamel, a stable viscosity and a constant consistency. The alkylated hydroxyaromatics can be used advantageously in wire enamel compositions for coating of electric and electronic components and equipment, especially copper wires.

DRAWINGS

The structure of a microreactor for performance of the process according to the invention is described in detail with reference to drawings.

Figure 2:
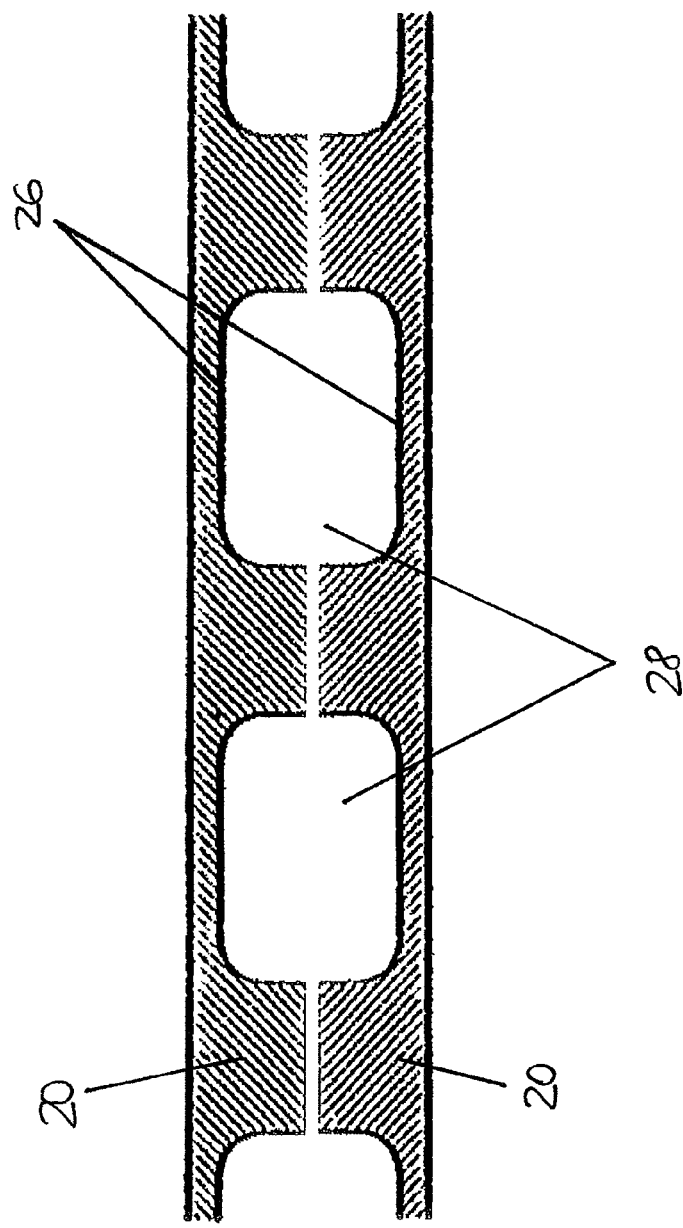

The figures show:

FIG. 1 a schematic diagram of the microreactor in section view,

FIG. 2 a schematic diagram of microstructured plates which form microchannels.

EMBODIMENT

FIG. 1 shows one embodiment of a microreactor 10 in section view. The reactants are converted to the vaporous state by means of an evaporator 12. A feed line 14 is used to pass the gas to the inlet orifice 22 in the microreactor 10. The distributor 16 in the region upstream of the microreactor unit 18 provides space in which the gas is distributed. Subsequently, the gas is passed through the microreactor unit 18, which is shown only schematically in FIG. 1. The hydroxyaromatics prepared are obtained at the outlet orifice 24.

The microreactor unit 18 of FIG. 1 is formed from microstructured plates 20 lying one on top of another. A cross section of two microstructured plates 20 lying one on top of the other is shown by way of example in FIG. 2. The two plates 20 each have complementary recesses 26 on one side and are aligned with respect to one another so as to form a multitude of microchannels 28. The profile of the microchannels 28 corresponds to a rectangle with rounded corners. As indicated in FIG. 1, in a microreactor unit 18, a multitude of microstructured plates 20 aligned with respect to one another is accommodated in a housing 30 of the microreactor 10.

These form microchannels 28, in which the chemical reaction takes place, running from an inlet orifice 22 to an outlet orifice 24.

EXAMPLES

The invention is described in detail by examples which follow.

In the examples, a microreactor according to FIGS. 1 and 2 is used. The microreactor is manufactured from 1.4742 stainless steel. In the microreactor units, 12 microchannels are provided per microstructured plate, and the microchannels have a lateral extent of (0.6×0.4) mm². For a length of the microchannels of 100 mm, there is accordingly a total volume of 0.288 ml for two microstructured plates. The microchannels are also coated as described above by washcoating with an alumina catalyst. For this purpose, the Puralox Sba200 catalyst from Sasol is used, which has the following properties:

| Specific internal surface area (BET) | 206 m³/g |
| Bulk density | 0.62 ml/g |
| $Al_2O_3$ content | 97.1% |
| $SiO_2$ content | 68 ppm |
| Alkali metal and alkaline earth metal content | 20 ppm. |

The microreactor is kept at a temperature of 470° C. by means of heating cartridges and heating collars for insulation, and a maximum temperature of 450° C. is established over the catalyst.

Comparative Example 1

A mixture of methanol and phenol in a molar ratio of 1 is fed by means of a metering pump at standard pressure and a flow rate of 0.1 ml/min is fed into a tubular reactor with an external diameter of 6 mm. The catalyst is an alumina catalyst which is present in the fixed bed. The reactor is kept at a temperature of 465° C., and a maximum temperature of 450° C. is established over the catalyst.

The modified residence time describes the mass of the catalyst per unit volume flow rate and is 0.71 g/h/l for the tubular reactor. The results for the alkylation of phenol with methanol are shown in Table 1.

TABLE 1

Results of the alkylation of phenol with methanol in a tubular reactor.

| Phenol [%] | Methanol | o-cresol | m-/p-cresol | 2,6-xylenol | Further xylenols | Trimethyl-phenols | Anisole | Water |
|---|---|---|---|---|---|---|---|---|
| 32.0 | 0.0 | 29.7 | 3.1 | 13.9 | 4.8 | 5.9 | 0.0 | 10.6 |

Example 1

A mixture of methanol and phenol in a molar ratio of 1 is fed through a preheater into a microreactor by means of a metering pump at standard pressure and a flow rate of 0.1 ml/min.

The composition of the reaction products is reproduced in Table 2.

TABLE 2

Results of the alkylation of phenol with methanol in a microreactor.

| Phenol [%] | Methanol | o-cresol | m-/p-cresol | 2,6-xylenol | Further xylenols | Trimethyl-phenols | Anisole | Water |
|---|---|---|---|---|---|---|---|---|
| 27.7 | 0.0 | 31.2 | 3.4 | 12.7 | 6.3 | 4.3 | 2.3 | 12.1 |

The modified residence time is $7.7 \cdot 10^{-2}$ gh/l. Compared to the above-described example of a tubular reactor, the microreactor has a residence time smaller by a factor of 9.2. In addition, the o-cresol to phenol ratio for the microreactor is a factor of 1.21 higher than for the tubular reactor. It is accordingly possible to achieve a better space-time yield with a microreactor.

Comparative Example 2

A mixture of ethanol and phenol in a molar ratio of 1 is fed into a tubular reactor with an external diameter of 6 mm by means of a metering pump at standard pressure and a flow rate of 0.1 ml/min. The reactor is kept at a temperature of 375° C., and a maximum temperature of 350° C. is established over the catalyst. The modified residence time is 0.68 gh/l, and the composition of the reaction products is reproduced in Table 3.

TABLE 3

Results of the alkylation of phenol with ethanol in a tubular reactor.

| Phenol [%] | Ethanol | 2-Ethyl-phenol | 3-/4-Ethyl-phenol | Polyalkylated phenols | Phenetole | Water |
|---|---|---|---|---|---|---|
| 24.16 | 1.54 | 32.07 | 5.83 | 26.16 | 0.0 | 10.24 |

Example 2

A mixture of ethanol and phenol in a molar ratio of 1 is fed through a preheater into a microreactor by means of a metering pump at standard pressure and a flow rate of 0.1 ml/min.

The reactor is kept at a temperature of 425° C., and a maximum temperature of 405° C. is established over the catalyst. The modified residence time is $7.7 \cdot 10^{-2}$ gh/l and is thus smaller by a factor of 8.8 compared to the tubular reactor. The composition of the reaction products is shown in Table 4. Compared to the tubular reactor, the result is a lower proportion of by-products in the microreactor in spite of a lower modified residence time.

TABLE 4

Results of the alkylation of phenol with ethanol in a microreactor.

| Phenol [%] | Ethanol | 2-Ethyl-phenol | 3-/4-Ethyl-phenol | Polyalkylated phenols | Phenetole | Water |
|---|---|---|---|---|---|---|
| 45.15 | 11.10 | 18.89 | 1.75 | 14.63 | 0.43 | 8.05 |

Comparative Example 3

A mixture of 2-propanol and phenol in a molar ratio of 1 is fed into a tubular reactor with an external diameter of 6 mm by means of a metering pump at standard pressure and a flow rate of 0.2 ml/min. The reactor is kept at a temperature of 415° C., and a maximum temperature of 400° C. is established over the catalyst. The modified residence time is 0.68 gh/l. The composition of the reaction products is reproduced in Table 5.

TABLE 5

Results of the alkylation of phenol with 2-propanol in a crude reactor.

| Phenol [%] | 2-Propanol | 2-Isopropyl-phenol | 3-/4-Isopropyl-phenol | Polyalkylated phenols | Isopropoxy-phenol | Water |
|---|---|---|---|---|---|---|
| 56.25 | 14.44 | 10.53 | 0.79 | 0 | 6.47 | 11.56 |

Example 3

A mixture of 2-propanol and phenol in a molar ratio of 1 is fed through a preheater into the microreactor by means of a metering pump at standard pressure and a flow rate of 0.1 ml/min.

The microreactor is kept at a temperature of 370° C., and a maximum temperature of 385° C. is established over the catalyst. The modified residence time is $8.1 \cdot 10^{-2}$ gh/l and is thus smaller by a factor of 8.4 compared to the tubular reactor. The composition of the reaction products is reproduced in Table 6.

TABLE 6

Results of the alkylation of phenol with 2-propanol in a microreactor.

| Phenol [%] | 2-Propanol | 2-Isopropyl-phenol | 3-/4-Isopropyl-phenol | Polyalkylated phenols | Isopropoxy-phenol | Water |
|---|---|---|---|---|---|---|
| 68.43 | 9.25 | 7.32 | 0.93 | 0 | 0.10 | 13.97 |

The invention claimed is:

1. A process for preparing alkylated hydroxyaromatics by heterogeneous catalytic reaction of hydroxyaromatics with $C_1$-$C_4$-alkanols in a microreactor,
wherein the hydroxyaromatics comprise at least one phenol compound selected from the group consisting of phenol, o-cresol, m-cresol, p-cresol, xylenols, trimethylphenols, tetramethylphenols, ethylphenols, diethylphenols, triethylphenols, iso-propylphenols, di-iso-propylphenols, tri-iso-propylphenols, tetra-iso-propylphenols, n-propylphenols, di-n-propylphenols, tri-n-propylphenols, tetra-n-propylphenols, tert-butylphenols, di-tert-butylphenols, tri-tert-butylphenols, and tetra-tert-butylphenols and
wherein the $C_1$-$C_4$-alkanols used are methanol, ethanol, n-propanol, isopropanol, or mixtures thereof;
said process comprising the steps of:
first, providing at least one microreactor unit formed from 2 to 10 plates which lie one on top of the other and have surface recesses that form microchannels, said microchannels being 50 mm to 150 mm in length, then
a) introducing the hydroxyaromatic and at least one compound selected from the group consisting of $C_1$-$C_4$-alkanols as reactants into at least one inlet orifice of the microreactor comprising at least one said microreactor unit,
b) passing the reactants through at least one microreactor unit of the microreactor at a temperature of from 300 to 600° C., said unit comprising
a multitude of microchannels, said microchannels having a maximum lateral extent of less than 0.6 mm, and
a heterogeneous catalyst being incorporated in the microchannels for conversion of the reactants, wherein said heterogeneous catalyst is introduced into the microchannels by washcoating the plates and optionally impregnating the washcoat with an active component, and
c) passing the hydroxyaromatics prepared out through at least one outlet orifice of the microreactor.

2. The process according to claim 1, characterized in that the heterogeneous catalyst comprises a solid support.

3. The process according to claim 2, characterized in that the solid support comprises one or more components from the group consisting of inorganic oxides, carbon, polymers, clay, a zeolite or mesoporous solids.

4. The process according to claim 2, characterized in that the heterogeneous catalyst comprises an active component on the solid support.

5. The process according to claim 1, characterized in that the heterogeneous catalyst consists essentially of alumina.

6. The process according to claim 1, characterized in that the reactants are in the liquid phase, in the gaseous phase or in biphasic form.

* * * * *